US010300307B2

(12) United States Patent
Hynynen et al.

(10) Patent No.: US 10,300,307 B2
(45) Date of Patent: May 28, 2019

(54) FOCUSED ULTRASOUND SYSTEM FOR SMALL BORE IMAGING (71) Applicants: Kullervo Hynynen, Toronto (CA); Anthony Chau, Toronto (CA); Rajiv Chopra, Coppell, TX (US)

(72) Inventors: Kullervo Hynynen, Toronto (CA); Anthony Chau, Toronto (CA); Rajiv Chopra, Coppell, TX (US)

(73) Assignee: Sunnybrook Research Institute, Toronto (CA)

( * ) Notice: Subject to any disclaimer, the term of this patent is extended or adjusted under 35 U.S.C. 154(b) by 558 days.

(21) Appl. No.: 14/785,531

(22) PCT Filed: Apr. 14, 2014

(86) PCT No.: PCT/US2014/033973
§ 371 (c)(1),
(2) Date: Oct. 19, 2015

(87) PCT Pub. No.: WO2014/172265
PCT Pub. Date: Oct. 23, 2014

(65) Prior Publication Data
US 2016/0067527 A1    Mar. 10, 2016

Related U.S. Application Data
(60) Provisional application No. 61/813,830, filed on Apr. 19, 2013.

(51) Int. Cl.
A61B 8/00    (2006.01)
A61N 7/02    (2006.01)
(Continued)

(52) U.S. Cl.
CPC ............ *A61N 7/02* (2013.01); *A61B 5/055* (2013.01); *G01R 33/4814* (2013.01);
(Continued)

(58) Field of Classification Search
CPC ............ A61N 7/02; A61N 2007/0091; G01R 33/4814; A61B 5/055; A61B 2090/3762;
(Continued)

(56) References Cited

U.S. PATENT DOCUMENTS 5,735,282 A    4/1998  Hossack
2002/0111569 A1   8/2002  Rosenschein et al.
(Continued)

OTHER PUBLICATIONS

International Search Report and Written Opinion dated Sep. 23, 2014 in connection with PCT/US2014/033973.

*Primary Examiner* — Peter Luong
(74) *Attorney, Agent, or Firm* — Quarles & Brady LLP (57) ABSTRACT A focused ultrasound ("FUS"} system capable of use in a small bore imaging system, such as a small bore magnetic resonance imaging ("MRI"} system is provided. The FUS system generally includes an ultrasound transducer whose position is adjusted by a positioning system. The positioning system is sized to fit within the bore of the small bore imaging system. For instance, the positioning system can fit within a diameter of 150 millimeters or less.

11 Claims, 6 Drawing Sheets (51) Int. Cl.
   *A61B 5/055* (2006.01)
   *G01R 33/48* (2006.01)
   *A61B 6/00* (2006.01)
   *A61N 7/00* (2006.01)
   *A61B 90/00* (2016.01)

(52) U.S. Cl.
   CPC .......... *A61B 6/4417* (2013.01); *A61B 6/508* (2013.01); *A61B 8/4416* (2013.01); *A61B 2090/374* (2016.02); *A61B 2090/3762* (2016.02); *A61N 2007/0091* (2013.01)

(58) Field of Classification Search
   CPC . A61B 2090/374; A61B 8/4416; A61B 6/508; A61B 6/4417
   See application file for complete search history.

(56) References Cited

U.S. PATENT DOCUMENTS

| | | | | |
|---|---|---|---|---|
| 2007/0253910 A1* | 11/2007 | Ahrens | .................. | A61B 5/411 424/9.34 |
| 2009/0035218 A1* | 2/2009 | Ross | ....................... | A61B 5/415 424/9.1 |
| 2010/0125192 A1 | 5/2010 | Chopra et al. | | |

* cited by examiner

FOCUSED ULTRASOUND SYSTEM FOR SMALL BORE IMAGING

CROSS-REFERENCE TO RELATED APPLICATIONS

This application represents the national stage entry of PCT International Application No. PCT/US2014/033973 filed on Apr. 14, 2014, which claims the benefit of U.S. Provisional Patent Application Ser. No. 61/813,830, filed on Apr. 19, 2013, the disclosures of which are hereby incorporated by reference in their entirety for all purposes.

BACKGROUND OF THE INVENTION

The field of the invention is systems and methods for focused ultrasound. More particularly, the invention relates to a focused ultrasound system capable of use in small bore imaging systems.

The present invention relates generally to a system and method of focused ultrasound application and, more particularly, to a focused ultrasound system that provides precise spatial positioning under the guidance of a medical imaging system to deliver focused ultrasound to a target location. More specifically, the present invention is a focused ultrasound ("FUS") system in which the target volume(s) for sonication are determined using an imaging apparatus.

Focused ultrasound therapy involves delivering ultrasound energy to localized regions of tissue from externally (non-invasive) or internally (minimally-invasive) located transducers. The amount of ultrasound energy delivered to tissue dictates the nature of the biologic effect produced at that location. At high intensities with continuous exposure, ultrasound energy can generate enough heat to cause irreversible thermal damage through coagulation. As the exposure is reduced in duty cycle to short pulses, the mechanical energy associated with ultrasound dominates and can be used to generate a range of bio-effects, including: vascular occlusion or hemorrhage, permeation of cells, and tissue-homogenization. The combination of FUS with microbubbles can generate additional bio-effects, including sonoporation and increasing of the permeability of the blood brain barrier.

Often, imaging with small animal models is performed in customized systems designed for these species. In order to maximize signal to noise ratio and sensitivity, these systems are generally designed specifically for rodents, and as a result have small openings or bores. As an example, high-field MRI systems have bore diameters of 5-20 cm, which is sufficient for a mouse or rat, but makes insertion of a focused ultrasound system challenging.

It would therefore be desirable to have a focused ultrasound system that was capable of exposing targets defined using dedicated small animal imaging systems having small bores, such as bores that are smaller than 154 millimeters.

SUMMARY OF THE INVENTION

The present invention overcomes the aforementioned drawbacks by providing a focused ultrasound system that fits within the bore of small bore imaging systems, which can have a bore diameter of less than 150 millimeters.

It is an aspect of the invention to provide a focused ultrasound system capable of use in a small bore imaging system. The focused ultrasound system includes an ultrasound transducer, a positioning system, and a control system in communication with the positioning system. The ultrasound transducer is configured to emit a beam of focused ultrasound energy toward a subject, and is coupled to the positioning system. The positioning system is capable of translating the position of the ultrasound transducer in at least one direction. For instance, the positioning system is capable of translating the position of the ultrasound transducer in a first horizontal direction and a second horizontal direction, such as a lateral direction and a longitudinal direction. The positioning system is sized to fit within a bore of a small bore imaging system, such as a bore of 150 millimeters or less. The control system controls the positioning system so as to adjust the position of the ultrasound transducer to localize a focal spot of the beam of focused ultrasound energy within a target location in the subject.

It is an aspect of the invention that the positioning system include a motor assembly having a first motor capable of adjusting a position of the ultrasound transducer in a first horizontal direction and a second motor capable of adjusting a position of the ultrasound transducer in a second horizontal direction. The first motor and the second motor may be rotated about a longitudinal axis of the motor assembly relative to each other so as to fit both motors within the bore of a small bore imaging system.

It is an aspect of the invention that the positioning system include a transducer mounting assembly that includes a transducer support configured to securely mount the ultrasound transducer, an upper guide plate positioned on an upper surface of the transducer support, and a lower guide plate positioned on a lower surface of the transducer support.

It is an aspect of the invention that the upper guide plate and the lower guide plate are capable of moving relative to one another to adjust the position of the ultrasound transducer in the lateral direction, and that the upper guide plate and the lower guide plate are capable of moving synchronously to adjust the position of the ultrasound transducer in the longitudinal direction.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
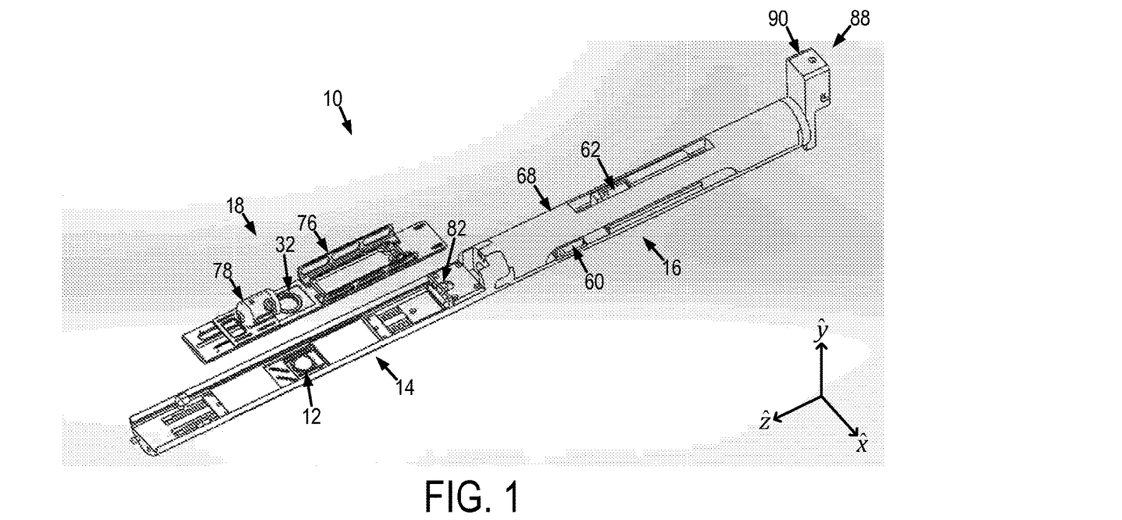
FIG. 1 illustrates a focused ultrasound system of the present invention that is capable of use in a small bore imaging system.
Figure 2:
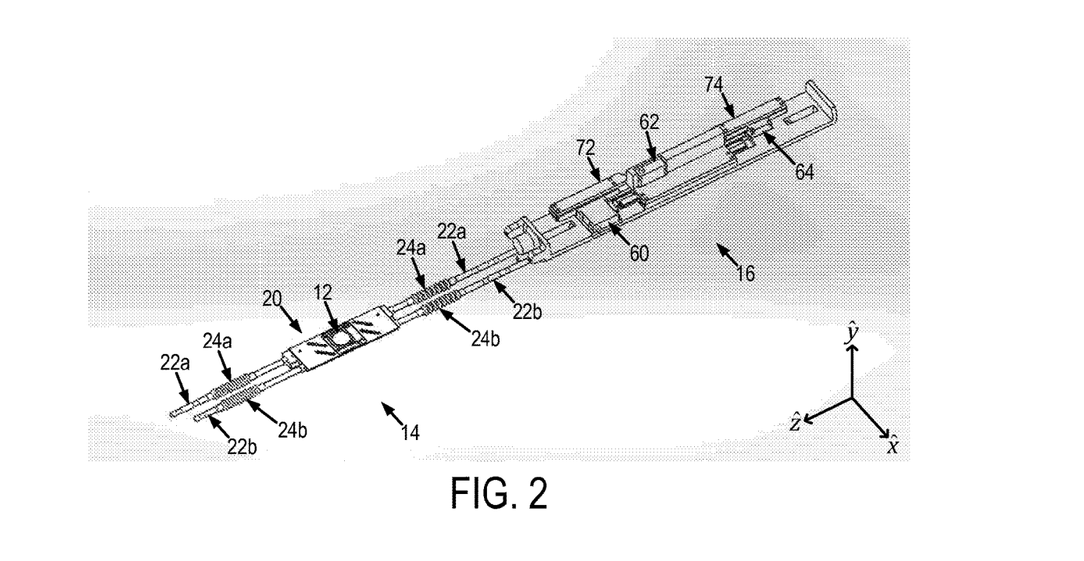
FIGS. 2-4 illustrate a positioning system that forms a part of the focused ultrasound system of FIG. 1.

Described here is a focused ultrasound system capable of use in a small bore imaging system, such as a small bore magnetic resonance imaging ("MRI") system, computed tomography ("CT") system, positron emission tomography ("PET") system, single photon emission computed tomography ("SPECT") system, and so on. As illustrated in FIG. 1, the focused ultrasound system 10 generally includes an ultrasound transducer 12, a positioning system 14 that includes a motor assembly 16, and a subject carrier 18. An alternative view of the focused ultrasound system is illustrated in FIG. 2.

In general, the positioning system 14 provides longitudinal and lateral motion of the ultrasound transducer 12. By way of example, lateral motion includes motion in the x-direction as indicated in FIGS. 1-9, and longitudinal motion includes motion in the z-direction as indicated in FIGS. 1-9. The positioning system 14 is capable of precisely positioning the ultrasound transducer 12 relative to a subject. For instance, the positioning system 14 can function to position the ultrasound transducer 12 in a desired location relative to one or more target locations that are identified in a subject by way of an image acquired with the small bore imaging system.

The ultrasound transducer 12 is configured to generate and emit focused, or unfocused, ultrasound energy towards a subject. The focusing can be achieved mechanically, such as by way of lenses and/or reflectors, or by manufacturing the transducer 12 to have a shape that intrinsically provides the desired focusing. Alternatively, the ultrasound transducer 12 can be a phased array device capable of electronic focusing and steering of the focal spot.

Figure 3:
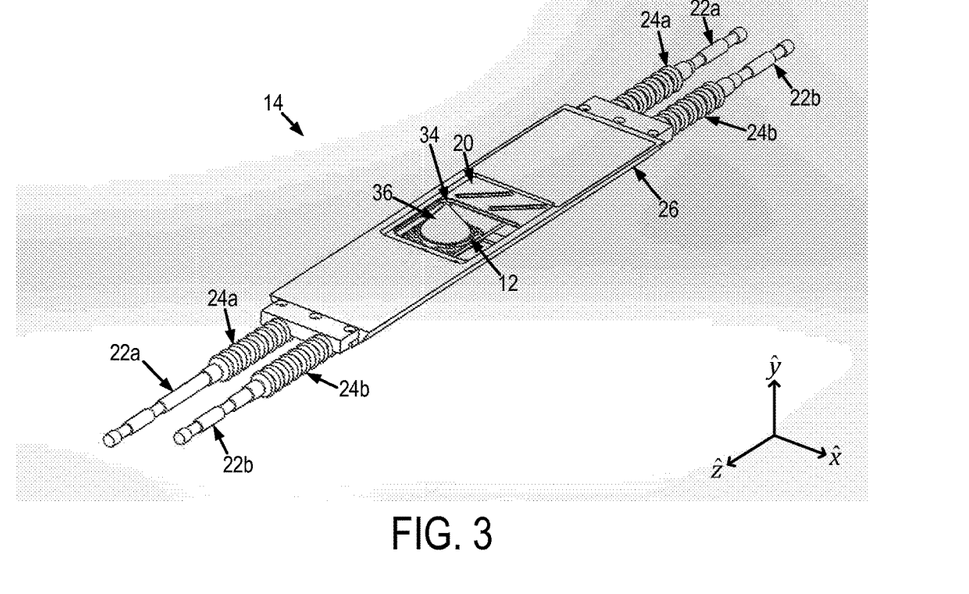
Figure 4:
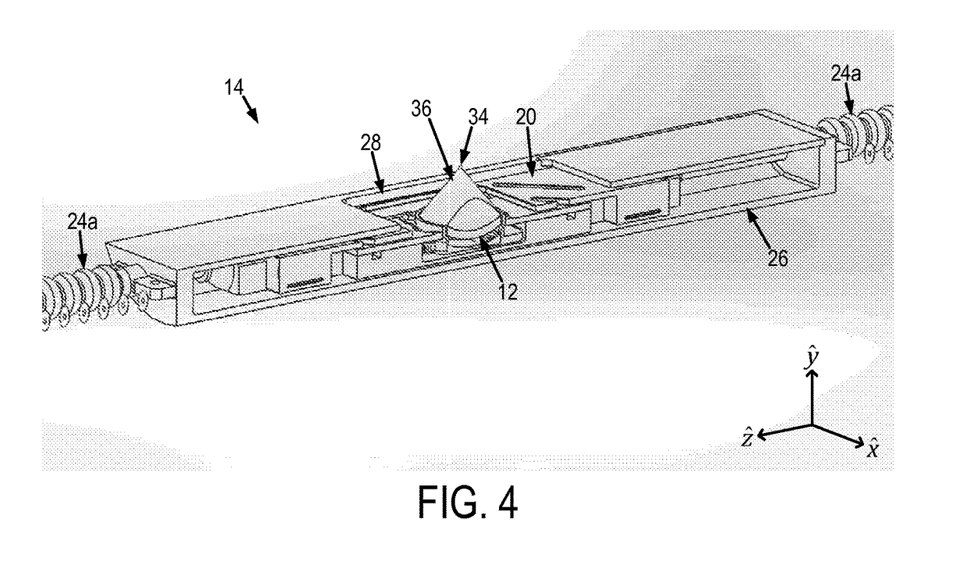

Referring to FIGS. 3 and 4, the positioning system 14 generally includes a moveable transducer mounting assembly 20 that is coupled to two drive rods 22a, 22b that are translated by a motor assembly (not shown in FIGS. 3 and 4). Bellows 24a, 24b can be coupled to the drive rods 22a, 22b to absorb lateral or offset movement of the drive rods 22a, 22b. The transducer mounting assembly 20 is preferably positioned within a tank 26 that has an opening 28 through which ultrasound energy 36 is transmitted to a subject. The opening 28 may constitute, for example, an acoustic window. The tank 26 is filled with a fluid, such as degassed water, that provides good acoustic coupling of the subject to the transducer 12.

The positioning system 14 is capable of precisely positioning a focal spot 34 of ultrasound energy 36 by appropriately positioning the ultrasound transducer 12. Preferably, the positioning system 14 is composed of non-magnetic materials so that the positioning system 14 is compatible for use with an MRI system.

Figure 8:
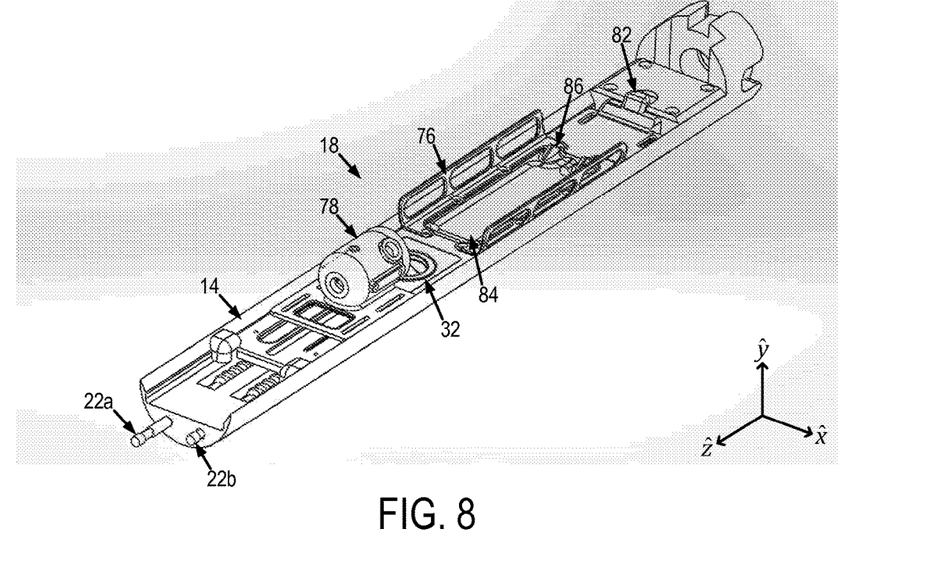
FIGS. 8 and 9 illustrate a subject carrier coupled to the positioning system of FIGS. 2-4.
Figure 9:
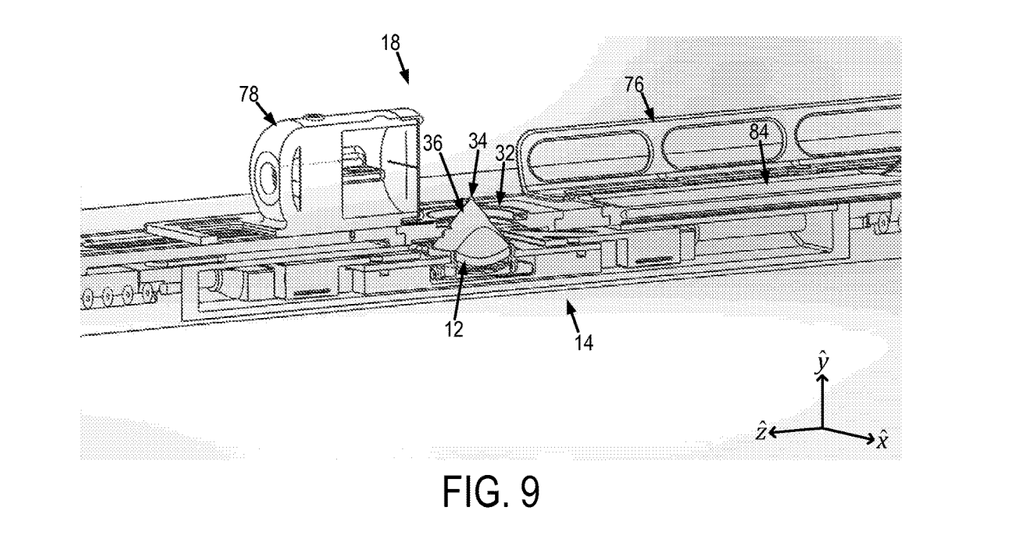

In some configurations for use with an MRI system, a radio frequency ("RF") coil 32 can be arranged in the opening 28 of the tank 26 (see FIGS. 8 and 9). By way of example, the RF coil 32 is a single-loop RF receive coil that can be used to acquire magnetic resonance signals, from which an image can be reconstructed.

Figure 5:
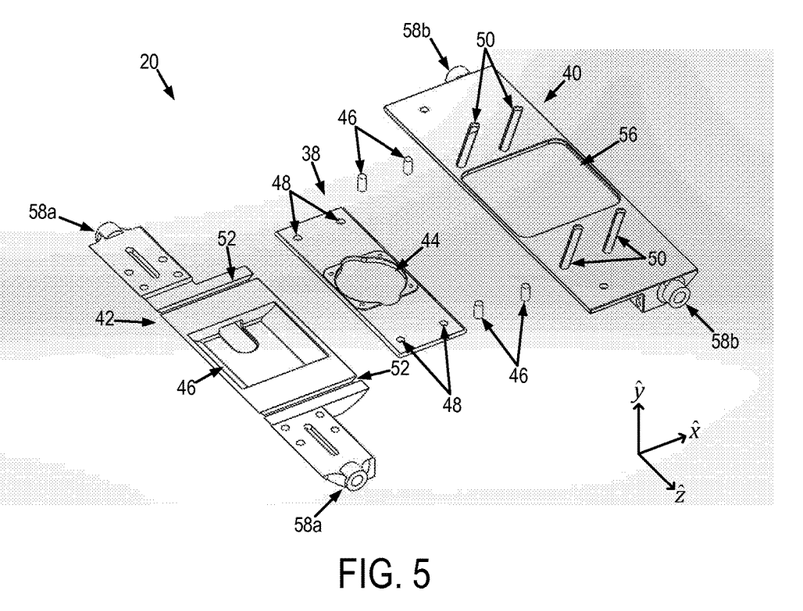
FIG. 5 illustrates a transducer mounting assembly that forms a part of the positioning system of FIGS. 2-4.

Referring now to FIG. 5, the transducer mounting assembly 20 generally includes a transducer support 38 arranged between and coupled to an upper guide plate 40 and a lower guide plate 42. The transducer support plate 38 includes an aperture 44 that is sized to receive the transducer 12 and is capable of securely supporting the transducer 12 in the transducer mounting assembly 20. The lower guide plate 42 includes a cavity 46 that is sized to receive the ultrasound transducer 12 when the ultrasound transducer 12 is mounted to the transducer support 38.

Pins 46 are positioned in holes 48 in the transducer support plate 38. The pins 46 engage guide channels 50 in the upper guide plate 40 and guide channels 52 in the lower guide plate 42.

The upper guide plate 40 includes an opening 56 that allows ultrasound energy emitted from the ultrasound transducer 12 to be delivered to the subject. The opening 56 is sized to be larger than the aperture 44 in the transducer support plate 38 such that a full range of lateral motion of the ultrasound transducer 12 can be achieved within the confines of the bore of a small bore imaging system. Particularly, the size of the opening 56 and the configuration of the transducer mounting assembly 20 allow for the transducer support plate 38 to traverse the full lateral dimension of the focused ultrasound system 10 without any components of the positioning system 14 extending beyond the spatial extent of the focused ultrasound system 10, which would impinge upon the small bore of the imaging system during use.

The upper guide plate 40 and the lower guide plate 42 are coupled to the drive rods 22a, 22b of the positioning system 14 by way of couplings 58a, 58b. For example, the upper guide plate 40 can be coupled to drive rod 22b by way of couplings 58b, and the lower guide plate 42 can be coupled to drive rods 22a by way of couplings 58a.

Figure 6:
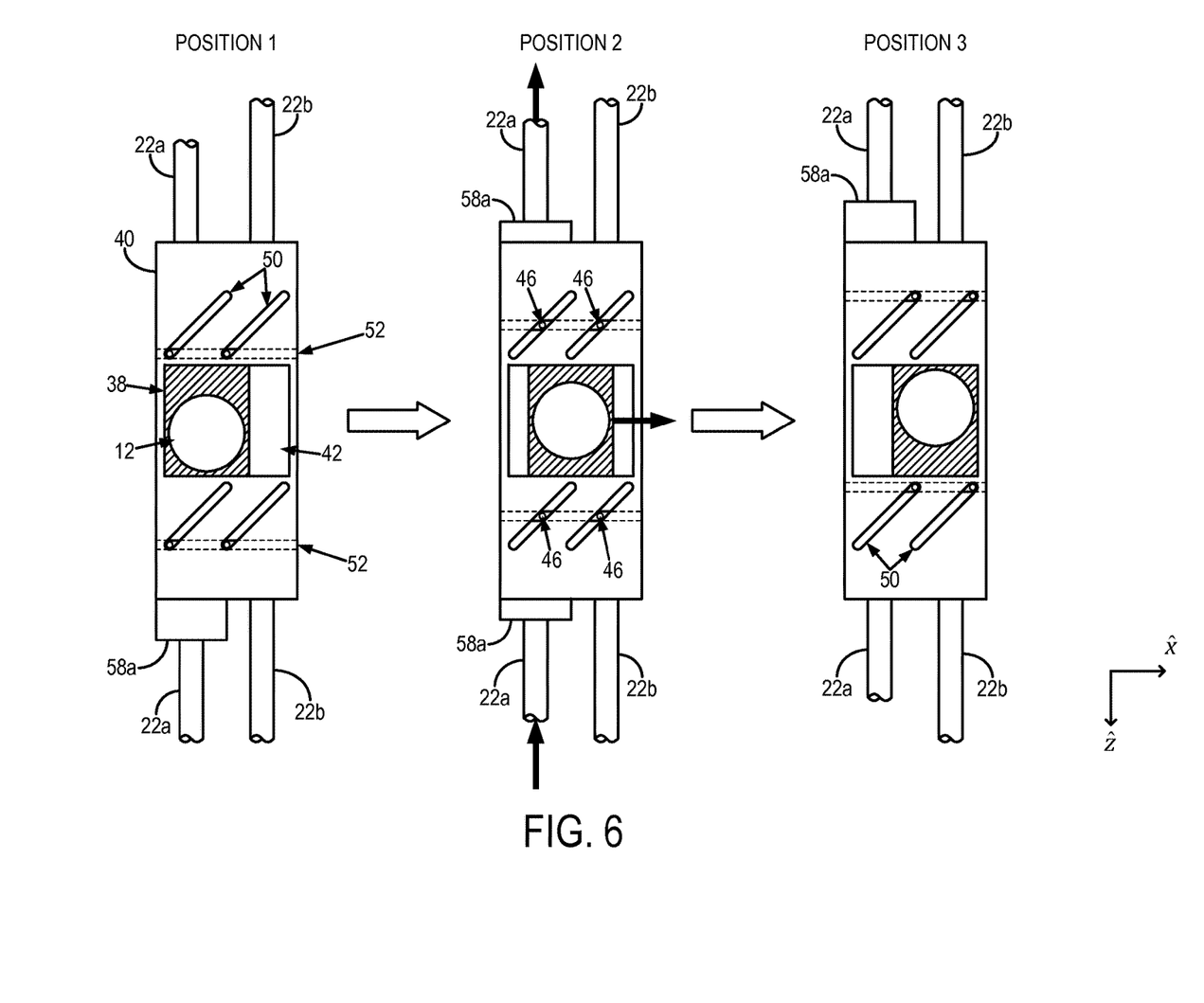
FIG. 6 illustrates adjusting the position of an ultrasound transducer using the position system of FIGS. 2-4.

The position of the ultrasound transducer 12 is changed by the relative motion of the upper guide plate 40 and the lower guide plate 42. The motion of the guide plates 40, 42 is provided by the drive rods 22a, 22b, which are coupled to the transducer mounting assembly 20 as described above. Differential motion of the drive rods 22a, 22b provides lateral motion of the transducer support plate 38, and thereby the ultrasound transducer 12, and synchronous motion of the drive rods 22a, 22b provides longitudinal motion of the transducer. As illustrated in FIG. 6, when drive rod 22a is moved, as indicated by the thick black arrows, and drive rod 22b is kept stationary, the transducer support 38 is moved laterally, as indicated by the thick black arrow indicating motion in the x-direction.

Figure 7:
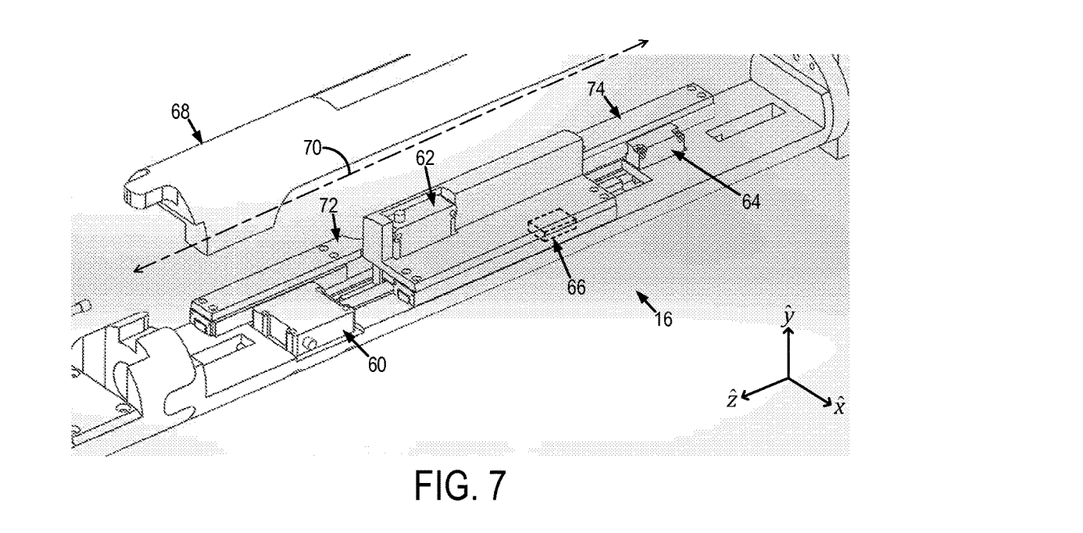
FIG. 7 illustrates a motor assembly that forms a part of the positioning system of FIGS. 2-4.

Referring to FIG. 7, the motor assembly 16 generally includes two motors 60, 62 capable of longitudinally translating the drive rods 22a, 22b. The motors 60, 62 are controlled by motor controllers in a control system 108 (see FIG. 10) described below. Also included in the motor assembly 16 are motion encoders 64, 66 that are associated with each of the motors 60, 62 to provide for precise motion control. The motion encoders 64, 66 are capable of monitoring the location of the positioning system 14 by sensing the linear translation of the drive rods 22a, 22b. As such, the precise position of the ultrasound transducer 12 within the coordinate system of the positioning system 14 can be determined by way of the motion encoders 64, 66 and their detection of any changes in the position of the drive rods 22a, 22b.

The motors 60, 62 and motion encoders 64, 66 are housed within a housing 68 that is sized to fit within the bore of a small bore imaging system. By way of example, the housing can be sized to fit within a bore having a diameter of 150 mm or less.

By way of example, the motors 60, 62 are linear piezomotors, such as piezoelectric or piezoceramic actuators. Alternatively, the motors 60, 62 can be other types of motors, such as rotary motors. Preferably, the motors 60, 62 are oriented such that one is rotated about the direction of the longitudinal axis 70 of the motor assembly 16 by ninety degrees with respect to the other. This orientation allows both motors 60, 62 to be contained within the small diameter necessary for the focused ultrasound system 10 to be capable of use in a small bore imaging system.

The motors 60, 62 are mechanically coupled to the drive rods 22a, 22b. By way of example, motor 60 can be coupled to drive rod 22a by way of slides 72, 74, which are mechanically coupled and synchronized to the motor 60. Similarly, motor 62 can be coupled to drive rod 22b by way of a plate (not shown) that is mechanically coupled to the motor 62.

By way of example, for use with MRI systems, the motion encoders 64, 66 are optical encoders. Alternatively, for use with other imaging systems, the motion encoders 64, 66 can be optical encoders or magnetic encoders. For use with MRI systems, the motion encoders 64, 66 preferably include non-metallic encoding elements, such as a plastic or glass encoding strip for linear motion encoding. For use with other imaging systems, the motion encoders 64, 66 can include metallic encoding elements. The motion encoders 64, 66 can be either absolute or incremental encoders.

Figure 10:
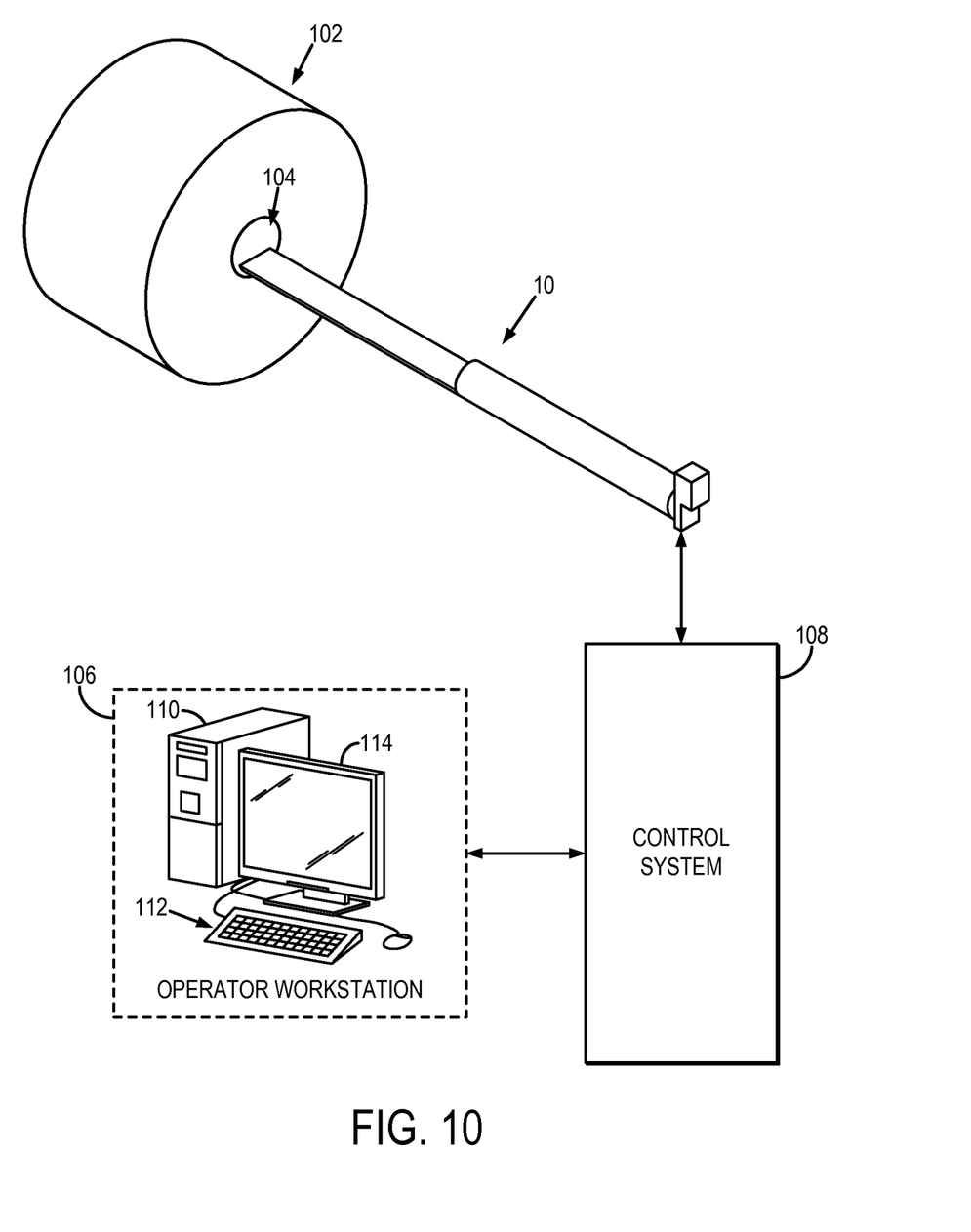
FIG. 10 is a block diagram of the focused ultrasound system of FIG. 1 configured for use in a small bore imaging system.

In response to a measured translation, the motion encoders 64, 66 output a signal indicative of an amount of translation. The monitored translation measured by the motion encoders 66, 64 is sent as feedback to the control system 108 via the output digital signal. The control system 108 is programmed to receive the measured translation feedback from motion encoders 64, 66 to determine any adjustment of positioning system 80 that may be necessary to compensate for any displacement in the drive rods 22a, 22b that may have been caused by an external force, such as the main magnetic field of an MRI magnet, a fluctuating magnetic field of the gradient coils in an MRI system, or another mechanical force. The measured translation feedback received by the control system 108 is processed and, in response thereto, control signals are generated and sent to motor controllers. The motor controllers can then drive the motors 60, 62 to translate the drive rods 22a, 22b such that the ultrasound transducer 12 is moved along one or more axes so as to "calibrate" the positioning system 14 and return the ultrasound transducer 12 to a proper location.

When used with an MRI system, the electrical cables powering the motors 60, 62 and motion encoders 64, 66 can be passed into the magnet room through filtered connectors on a grounded RF-penetration panel.

Referring to FIGS. 8 and 9, the subject carrier 18 serves to hold the subject in a fixed position during imaging and ultrasound exposures such that the target locations identified with imaging remain valid during focused ultrasound sonication. The subject carrier 18 is generally constructed as a removable sled that includes a subject table 76 on which the subject is positioned and a nose cone 78 capable of receiving the head of a small animal. The subject carrier 18 is capable of being coupled to the proximal end 80 of the positioning system 14 via a connection clip 82.

The subject table 76 may optionally include a heated pad 84 that includes channels through which a heated fluid is passed. The heated fluid is provided to the channels by way of a flow connection 86.

Fixation of the subject can be achieved through stereotactic methods, such as a bite bar, ear bars, or other features known to those familiar with the field including straps and restraints.

The subject carrier 18 can include physiological monitors to measure physiological signals, such as temperature, blood pressure, blood oxygen level, and heart rate. Preferably, the physiological monitors are composed of materials that are compatible with the imaging system.

Referring now to FIG. 10, a block diagram of an example focused ultrasound system 10 of the present invention in use with a small bore imaging system 102 is illustrated. The small bore imaging system 102 acquires images of a subject or object of interest, such as a small animal used for focused ultrasound therapy testing. The focused ultrasound system 10, or a portion thereof, is capable of being positioned adjacent to or within the bore 104 of the small bore imaging system 102. For instance, a coupling 90 at the proximal end 88 of the focused ultrasound system 10 can be used to couple the focused ultrasound system 10 to a patient table (not shown) such that the focused ultrasound system 10 can be advanced partially or wholly into the bore 104 of the small bore imaging system 102. As such, the subject, or a portion thereof, is positioned within the bore 104 of the small bore imaging system 102 during imaging.

An operator workstation 106 is used to control the small bore imaging system 102 and communicates with a separate control system 108 that enables an operator to control the focused ultrasound system 10. The operator workstation 106 generally includes a processor 110, a keyboard 112, and a display 114.

The control system 108 is programmed to determine positional coordinates of one or more target locations within a coordinate system of the small bore imaging system 102. These positional coordinates are then registered with a coordinate system of the positioning system 14. Once registered with the coordinate system of the positioning system 14, the positional coordinates of the target location(s) are sent as an input signal to the motor assembly 16 in the positioning system 14. The motor assembly 16 receives the positional coordinates and is actuated by control system 108 to position the ultrasound transducer 12 in proximity to target location such that ultrasound energy emitted from the ultrasound transducer 12 is focused at the target location.

The positioning system 14 is thus controlled by the control system 108 to allow for the intermittent or continuous repositioning of the ultrasound transducer 12 during an imaging procedure. This positional control of the ultrasound transducer 12 allows for the delivery of ultrasound energy to a plurality of target locations or points in rapid succession, such that a plurality of target points in a region of the subject or object of interest can be sonicated within a short timeframe. Thus, via the control of positioning system 14, the ultrasound transducer 12 can be translated to deliver ultrasound energy to a plurality of target points within a subject in any of a point exposure, scanned linear (1D, 2D) exposure, or raster scan (1D, 2D) exposure pattern, or along another continuous trajectory.

In one beneficial application, the focused ultrasound system 10 can be implemented for delivery of focused ultrasound to the brain of small animals. It is also recognized that the focused ultrasound system described here is also suitable for delivery of focused ultrasound to localized areas of an animal. Alternatively this system can also be used on inanimate objects.

Furthermore, while a preferred embodiment of the focused ultrasound system 10 is described in conjunction with an MRI system as the source of guidance of the focused ultrasound, guidance can also be achieved through use of other imaging technologies, such as x-ray imaging, CT, PET, SPECT, ultrasound, thermoacoustic imaging, photoacoustic imaging, optical imaging, or other imaging modalities capable of providing anatomical, functional, or physiological information. Guidance of the focused ultrasound can alternatively be provided by an operator or another computer having data stored thereon.

The present invention has been described in terms of one or more preferred embodiments, and it should be appreciated that many equivalents, alternatives, variations, and modifications, aside from those expressly stated, are possible and within the scope of the invention.

The invention claimed is:

1. A focused ultrasound system capable of use in a small bore imaging system, comprising:
   an ultrasound transducer configured to emit a beam of focused ultrasound energy toward a subject;
   a positioning system sized to fit within a bore of a small bore imaging system and capable of positioning the ultrasound transducer to localize the beam of focused ultrasound energy within a target location in the subject, the positioning system comprising
   a motor assembly configured to translate the ultrasound transducer along at least one direction, wherein the bore of the small bore imaging system has a diameter less than 150 millimeters;
   a transducer mounting assembly coupled to the ultrasound transducer and configured to selectively adjust a position of the ultrasound transducer in a lateral direction such that the ultrasound transducer can be translated along a full lateral dimension of the focused ultrasound system without extending beyond a spatial extent of the focused ultrasound system; and
   a control system in communication with the positioning system and configured to control the motor assembly so as to position the ultrasound transducer to localize the beam of focused ultrasound energy within the target location in the subject.

2. The focused ultrasound system as recited in claim 1 in which the motor assembly comprises:
   a first motor capable of adjusting a position of the ultrasound transducer in a first horizontal direction; and
   a second motor capable of adjusting a position of the ultrasound transducer in a second horizontal direction;
   wherein one of the first horizontal direction and the second horizontal direction corresponds to the lateral direction.

3. The focused ultrasound system as recited in claim 2 in which the first motor and the second motor are rotated about a longitudinal axis of the motor assembly relative to each other.

4. The focused ultrasound system as recited in claim 2 in which the first motor and the second motor are linear piezomotors.

5. The focused ultrasound system as recited in claim 2 in which the positioning system further comprises a first drive rod coupled to the ultrasound transducer and the first motor, and a second drive rod coupled to the ultrasound transducer and the second motor.

6. The focused ultrasound system as recited in claim 2 in which the positioning system further comprise:
   a first motion encoder coupled to the first motor to measure the translation of the ultrasound transducer along the first horizontal direction; and
   a second motion encoder coupled to the second motor to measure the translation of the ultrasound transducer along the second horizontal direction.

7. The focused ultrasound system as recited in claim 6 in which the first motion encoder and the second motion encoder include an optical encoder.

8. A focused ultrasound system capable of use in a small bore imaging system, comprising:
   an ultrasound transducer configured to emit a beam of focused ultrasound energy toward a subject;
   a positioning system coupled to the ultrasound transducer and capable of translating a position of the ultrasound transducer in a lateral direction and a longitudinal direction, the positioning system being sized to fit within a bore of a small bore imaging system, wherein the bore of the small bore imaging system has a diameter less than 150 millimeters;
   a transducer mounting assembly coupled to the ultrasound transducer and configured to selectively adjust the position of the ultrasound transducer in the lateral direction such that the ultrasound transducer can be translated along a full lateral dimension of the focused ultrasound system without extending beyond a spatial extent of the focused ultrasound system; and
   a control system in communication with the positioning system and configured to control the positioning system so as to adjust the position of the ultrasound transducer to localize a focal spot of the beam of focused ultrasound energy within a target location in the subject.

9. The focused ultrasound system as recited in claim 8 in which the transducer mounting assembly is further configured to selectively adjusting the position of the ultrasound transducer in the longitudinal direction.

10. The focused ultrasound system as recited in claim 9 in which the transducer mounting assembly comprises:
    a transducer support configured to securely mount the ultrasound transducer;
    an upper guide plate positioned on an upper surface of the transducer support; and
    a lower guide plate positioned on a lower surface of the transducer support.

11. The focused ultrasound system as recited in claim 10 in which the upper guide plate and the lower guide plate are capable of moving relative to one another to adjust the position of the ultrasound transducer in the lateral direction, and in which the upper guide plate and the lower guide plate are capable of moving synchronously to adjust the position of the ultrasound transducer in the longitudinal direction.

* * * * *

UNITED STATES PATENT AND TRADEMARK OFFICE
CERTIFICATE OF CORRECTION

PATENT NO. : 10,300,307 B2
APPLICATION NO. : 14/785531
DATED : May 28, 2019
INVENTOR(S) : Kullervo Hynynen, Anthony Chau and Rajiv Chopra It is certified that error appears in the above-identified patent and that said Letters Patent is hereby corrected as shown below:

In the Claims

Claim 9:
"The focused ultrasound system as recited in claim 8 in which the transducer mounting assembly is further configured to selectively adjusting the position of the ultrasound transducer in the longitudinal direction."
Should read:
-- The focused ultrasound system as recited in claim 8 in which the transducer mounting assembly is further configured to selectively adjust the position of the ultrasound transducer in the longitudinal direction. --

Signed and Sealed this
Twenty-sixth Day of April, 2022

Katherine Kelly Vidal
*Director of the United States Patent and Trademark Office*